(12) United States Patent
O'Lenick et al.

(10) Patent No.: US 7,820,758 B1
(45) Date of Patent: Oct. 26, 2010

(54) POLYMERIC GLYCERIN SURFACTANTS

(76) Inventors: Kevin A. O'Lenick, 2170 Luke Edwards Rd., Dacula, GA (US) 30019; Anthony J. O'Lenick, Jr., 2170 Luke Edwards Rd., Dacula, GA (US) 30019

( * ) Notice: Subject to any disclaimer, the term of this patent is extended or adjusted under 35 U.S.C. 154(b) by 506 days.

(21) Appl. No.: 11/983,439

(22) Filed: Nov. 13, 2007

(51) Int. Cl.
*C08G 63/00* (2006.01)
(52) U.S. Cl. ............... 525/32.1; 525/35; 525/36; 525/41; 525/43; 528/361; 562/592
(58) Field of Classification Search ............... 528/361; 525/32.1, 35, 36, 41, 43; 524/112
See application file for complete search history.

(56) References Cited

U.S. PATENT DOCUMENTS

| | | | |
|---|---|---|---|
| 3,936,391 A | | 2/1976 | Gabby et al. |
| 6,207,724 B1 * | | 3/2001 | Hird et al. ............ 521/64 |
| 2003/0153787 A1 * | | 8/2003 | Carpenter et al. ......... 562/592 |

OTHER PUBLICATIONS

Cho et al Glycerol esters from the reaction of glycerol with dicarboxylic acid esters, Journal of Surfactants and Detergents, vol. 9, No. 2, pp. 147-152, 2006.*

* cited by examiner

*Primary Examiner*—Gregory Listvoyb

(57) ABSTRACT

The invention discloses a series of glycerin/succinate/alkyl succinate polyesters. These materials are high foaming detergents useful in the formulation of biodegradable, polyoxyalkylene free, cosmetic and personal care products.

8 Claims, No Drawings

POLYMERIC GLYCERIN SURFACTANTS

RELATED APPLICATIONS

None

FEDERAL SPONSORSHIP

None

FIELD OF THE INVENTION

The present invention is drawn to a series of polymeric compounds made by the reaction glycerin with anhydrides selected from the group consisting succinic anhydride, phthalic anhydride and alkenyl succinic anhydride. By selecting the proper ratios of glycerin to anhydrides, high foaming surfactants, free of polyoxyalkylene glycol can be prepared. These compounds are of great interest in the personal care market.

BACKGROUND OF THE INVENTION

The term surfactant is a coined contraction for "surface active agent". It refers to a class of materials that are amphillic, that is possess groups within one molecule that would be insoluble in each other if mixed separately. Most commonly these two groups are water soluble (hydrophilic) and oil soluble (lipophilic).

Standard surfactants, also called fatty surfactants, are commonly made from oil soluble groups like fatty alcohols, which are made soluble by reaction with ethylene oxide. Ethylene oxide is a reactive epoxide belonging to a class of compounds called oxiranes. When ethylene oxide is reacted with a fatty alcohol a more water soluble ether group is formed.

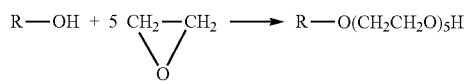

Polyoxyalkylene based surfactants have been known for many years and make up a class of compounds referred to as non-ionic surfactants. Recently, surfactants based upon PEG have become less desirable by consumers based upon the fact they are not considered green.

There has been a push to develop surfactants based upon natural, renewable, inexpensive and available raw materials. One such material is glycerin. As biodisel becomes more and more common in our national quest to limit dependence upon petroleum, glycerin becomes more available and less expensive. This is because glycerin is a by-product of the process. The polyester compounds of the present invention unlike many of the synthetic detergents in use today are biodegradable.

Glycerin has been used in a variety of applications, including polyglycerin used as a base to make esters. Polyglycerin esters are used as oils and not as foaming surfactants. Typical of the preparation of esters of polyglycerin is U.S. Pat. No. 3,936,391 to Gabby issued in 1976 teaches a Polyglycerol ester composition classified as imitation butter, margarine, cheese spreads, dips, frozen desserts including ice cream and sherbert, puddings, icings, salad dressings, sauces, and the like. It clearly is an oil and noty a water soluble surfactant.

The problem with using glycerin as a raw material to make high foaming surfactants is that the derivatives heretofore attempted have lack the water solubility that can be achieved when using PEG based products. Put another way the glycerin is a far less effective material at making fatty materials water-soluble.

The present invention addresses this long felt need for a surfactant based upon glycerin. Critical to the functioning of the present invention is the preparation of a poly ester of glycerin and an anhydride, linking the groups together, but equally important is the inclusion of an alkenyl succinic anhydride into the polyester in the proper ratio in order to build in domains of oil soluble groups. We have surprisingly found that if incorporated into the polyester, products with low levels of domains derived from alkenyl succinic anhydride produce copious foam.

Alkenyl succinic anhydrides are known materials. Perhaps the most important patent is U.S. Pat. No. 5,319,030, incorporated herein by reference, to Harrison et al not only teaches a process for the preparation of an alkenyl-substituted succinic anhydride, but also provides a review of alternate methods to make and hydrogenate these materials. Alkenyl-substituted succinic anhydrides have been prepared by two different processes, a thermal process (see, e.g., U.S. Pat. No. 3,361,673) and a chlorination process (see e.g., U.S. Pat. No. 3,172,892). The polyisobutenyl succinic anhydride ("PIBSA") produced by the thermal process has been characterized as a monomer containing a double bond in the product. Although the exact structure of chlorination PIBSA has not been definitively determined, the chlorination process PIBSA materials have been characterized as monomers containing either a double bond, a ring other than succinic anhydride ring and/or chlorine in the product. The analytical difficulties offered by analysis of both the succinic derivatives used as raw materials in the preparation of the compounds of the present invention and the complex oligomeric mixtures that result when the polymer is made makes the preferred method of claiming the polymers of the present invention product by process claims.

Polyesters of the present invention and their unique surfactant properties have been heretofore unknown in detergent sciences.

THE INVENTION

Summary of the Invention

The present invention is drawn to a series of polymeric compounds made by the reaction glycerin with anhydrides selected from the group consisting succinic anhydride, phthalic anhydride and alkenyl succinic anhydride. By selecting the proper ratios of glycerin to anhydrides, high foaming surfactants, free of polyoxyalkylene glycol can be prepared. These compounds are of great interest in the personal care market.

OBJECT OF THE INVENTION

The object of the present invention is to provide a class of glycerin based surfactants that are made by the esterification of glycerin, with alkenyl succinic anhydride (providing hydrophobicity), and one or more anhydride selected from the group consisting of succinic anhydride, or phthalic anhydride Another objective is a process of cleansing skin and hair comprising contacting the hair or skin with an effective cleansing concentration of the compounds of the present invention.

Other objectives will become clear as one reads and understands the disclosure.

DETAILED DESCRIPTION OF THE INVENTION

The compounds of the present invention are prepared by the following sequence:

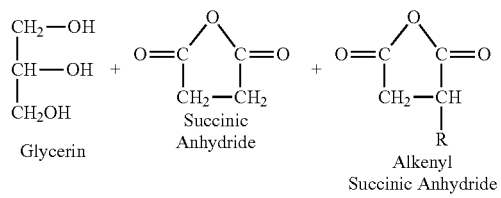

Glycerin    Succinic Anhydride    Alkenyl Succinic Anhydride

The mole ratio of the reaction is set so that there is always an excess of hydroxyl group relative to carboxyl group in the polyester. The preferred ratio is between 3 hydroxyl groups to 1 carboxyl group, to 2 hydroxyl groups to 1 carboxyl groups.

When the materials are added together they are heated to 120-150° C. and held for several hours. During this time the anhydride opens up and a carboxy ester is formed. In order to simplify the description of the reaction we have shown succinic anhydride as the only reactant. In reality the alkenyl succinic anhydride is also included to make a polymer with the desired hydrophobicity and surfactant property. R' is used in the reaction below and it is a mixture of H and R. That is the anhydride used to make the product is a mixture of alkenyl succinic anhydride and succinic anhydride.

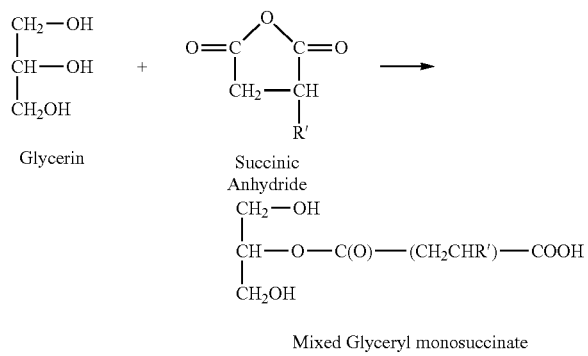

Glycerin    Succinic Anhydride

Mixed Glyceryl monosuccinate

R' is a mixture of H and alkenyl.

While we show the structure as having reacted at the center hydroxyl, there is actually a mixture of mono isomers and a relatively low concentration of di product, resulting in an oligomeric product.

As the temperature is increased to 180-190° C. the carboxyl groups react with to make polyester.

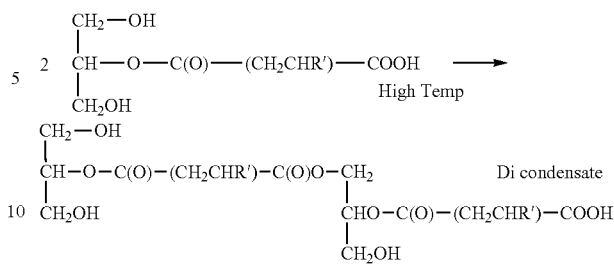

As the reaction proceeds the polyester continues to increase in molecular weight and the viscosity of the product increases. Additionally, and critically importantly to the reaction, the product becomes clear as the alkenyl succinic anhydride is incorporated by reaction into the polyester backbone.

The continued reaction is as follows;

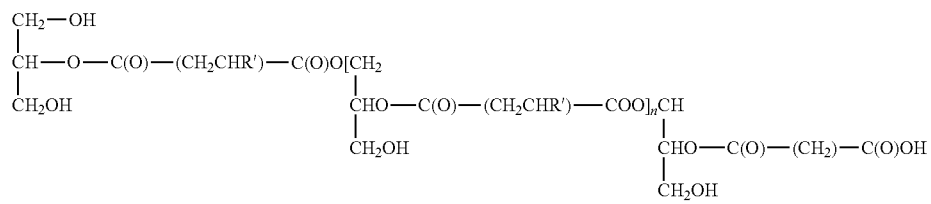

The resulting polymer is an A-(B)$_n$C wherein

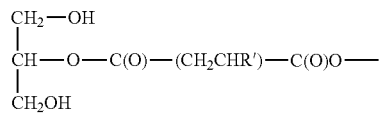

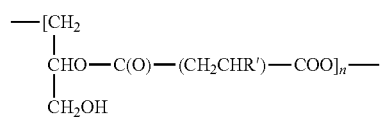

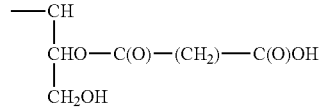

wherein

R' is a mixture of H, alkenyl and alkyl having 10 to 20 carbon atoms;

n is an integer ranging from 25 to 400.

The present invention is directed to a polymer made by the esterification reaction of (a) glycerin conforming to the following structure:

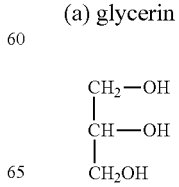

(b) succinic anhydride conforming to the following structure;

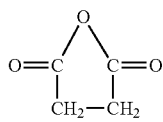

and (c) an alkenyl succinic anhydride conforming to the following structure:

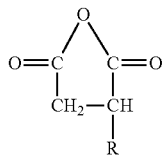

wherein
R is selected from alkyl, alkenyl and mixtures of thereof having 10 to 20 carbon atoms.

Preferred Embodiment

In a preferred embodiment R is alkyl having 10 to 20 carbon atoms

In another preferred embodiment R is alkenyl having 10 to 20 carbon atoms.

In a preferred embodiment the mole ratio of hydroxyl to carboxyl in the reactants ranges from 3:1 to 2:1.

In a more preferred embodiment the mole ratio of hydroxyl to carboxyl in the reactants is 3:1.

In a preferred embodiment R' is a mixture of R and H.

In a preferred embodiment R' is a mixture of R and H, wherein the ratio of R to H ranges from 1:5 to 1:20.

In a preferred embodiment R' is a mixture of R and H, wherein the ratio of R to H ranges from 1:10 to 1:15.

EXAMPLES

Raw Materials

A. Example 1

Glycerin

Glycerin is an item of commerce confirming to the following structure;

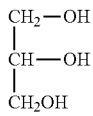

CAS no. 56-81-5

It is available from a variety of sources including Proctor and Gamble.

B. Example 2

Succinic Anhydride

Succinic anhydride conforming to the following structure;

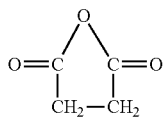

CAS No. 108-30-5

It is available from a variety of sources including Sigma Aldrich Corp. St. Louis, Mo.

C. Example 3-10

Alkenyl Succinic Anhydride

Alkenyl succinic anhydride conforming to the following structure:

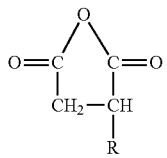

wherein

R is selected from alkyl, alkenyl and mixtures of thereof having 10 to 20 carbon atoms.

The products as prepared by reaction of alpha olefin and maleic anhydride result in a alkenyl compound

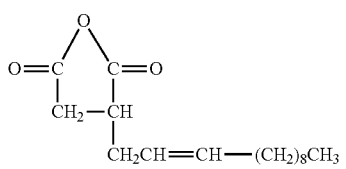

These compounds are hydrogenated to make alkyl compounds:

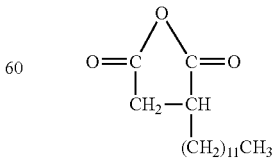

Alkyl and alkenyl succinic anhydrides are commercially available from a variety of sources including Humphery Inc.

| Example | Type | Carbon Atoms |
| --- | --- | --- |
| 3 | Alkenyl | C10 |
| 4 | Alkenyl | C12 |
| 5 | Alkenyl | C16 |
| 6 | Alkenyl | C20 |
| 7 | Alkyl | C10 |
| 8 | Alkyl | C12 |
| 9 | Alkyl | C16 |
| 10 | Alkyl | C20 |

Compounds of the Present Invention

To 100 grams of glycerin is added the specified number of grams of succinic anhydride, the specified number of grams of the specified of alkenyl succinic anhydride (example 3-10). The reaction mass is heated to 120-130° C. As reaction reaches 120° C. the batch becomes homogeneous. The temperature is held for three hours. The temperature is increased to 180-190° C. Water is distilled off and the reaction mass becomes thick. The batch clears as the reaction proceeds and the acid value decreases to theoretical.

The amount of water distilled off is used to calculate the "n" value.

| Example | Glycerin | Succinic Anhydride | Alkenyl succinic Example | Alkenyl succinic Grams | R' Alkyl:H | OH:COOH | n value* |
| --- | --- | --- | --- | --- | --- | --- | --- |
| 11 | 61.1 | 42.5 | 3 | 17.3 | 1:5 | 3:1 | 25 |
| 12 | 52.0 | 37.0 | 4 | 11.0 | 1:10 | 2:1 | 50 |
| 13 | 94.8 | 47.5 | 5 | 8.0 | 1:20 | 3:1 | 80 |
| 14 | 47.2 | 31.7 | 6 | 21.0 | 1:5 | 2:1 | 100 |
| 15 | 52.6 | 37.5 | 7 | 9.9 | 1:10 | 3:1 | 50 |
| 16 | 53.8 | 40.5 | 8 | 5.7 | 1:20 | 3:1 | 400 |
| 17 | 48.6 | 32.7 | 9 | 18.6 | 1:5 | 2:1 | 250 |
| 18 | 48.8 | 40.5 | 10 | 5.7 | 1:5 | 3:1 | 200 |
| 19 | 60.2 | 27.0 | 4 | 12.8 | 1:10 | 3:1 | 400 |
| 20 | 50.2 | 33.8 | 8 | 16.0 | 1:5 | 2:1 | 100 |

*calculated by water distilled off during reaction.

The products as prepared are viscous yellow liquids. They are subsequently cut with water to a solids level of between 25 and 50% by weight.

Applications

The products of the present invention are high foaming compounds that provide detergency and a very cosmetically appealing skin feel.

Foam

The foam characteristics are determined by (a) alkyl to hydrogen ratio and (b) the hydroxyl to carboxyl value. The higher the alkyl value, the more hydrophobic the product. The foam level peaks as the percentage of alkyl or alkenyl succinate increases to around 10% by weight. Above this the foam decreases and improved conditioning is noted. As the percentage by weight of alkyl or alkenyl succinate increases above 25% by weight a water insoluble product is encountered.

As the hydroxyl to carboxyl ratio is increased from 2:1 to 3:1 water solubility increases and humectancy is observed. The foam decreases as the hydroxyl to carboxyl ratio increases.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polymer conforming to the following structure;

$$A\text{-}(B)_n C$$

wherein

A is

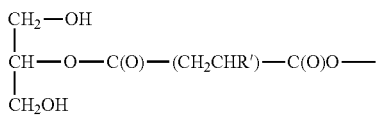

B is

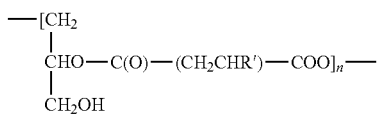

C is

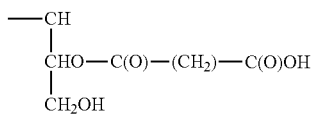

wherein

R' is a mixture of H and alkenyl and alkyl having 10 to 20 carbon atoms;

n is an integer ranging from 25 to 400.

2. A polymer of claim 1 wherein R' is a mixture of R and H.

3. A polymer of claim 2 wherein the ratio of R to H ranges from 1:5 to 1:20.

4. A polymer of claim 2 wherein the ratio of R to H ranges from 1:10 to 1:15.

5. A polymer of claim 2 wherein R is alkyl having 10 to 20 carbon atoms.

6. A polymer of claim 2 wherein R is alkenyl having 10 to 20 carbon atoms.

7. A polymer of claim 2 wherein the mole ratio of hydroxyl to carboxyl in the reactants ranges from 3:1 to 2:1.

8. A polymer of claim 2 wherein the ratio the mole ratio of hydroxyl to carboxyl in the reactants is 3:1.

* * * * *